(12) United States Patent
Chen et al.

(10) Patent No.: US 9,451,981 B2
(45) Date of Patent: Sep. 27, 2016

(54) SURGICAL TISSUE PROTECTION SHEATH

(71) Applicant: SPIWay LLC, Carlsbad, CA (US)

(72) Inventors: Eugene Chen, Carlsbad, CA (US);
Cang Lam, Irvine, CA (US)

(73) Assignee: SPIWay LLC, Carlsbad, CA (US)

( * ) Notice: Subject to any disclaimer, the term of this patent is extended or adjusted under 35 U.S.C. 154(b) by 0 days.

(21) Appl. No.: 14/630,463

(22) Filed: Feb. 24, 2015

(65) Prior Publication Data
US 2015/0164552 A1 Jun. 18, 2015

Related U.S. Application Data

(63) Continuation-in-part of application No. 13/798,990, filed on Mar. 13, 2013, now Pat. No. 8,986,201, which is a continuation-in-part of application No. 12/943,779, filed on Nov. 10, 2010, now abandoned, application No. 14/630,463, which is a continuation-in-part of application No. 13/760,971, filed on Feb. 6, 2013, now Pat. No. 9,011,326.

(60) Provisional application No. 61/730,588, filed on Nov. 28, 2012, provisional application No. 61/261,310, filed on Nov. 14, 2009, provisional application No. 61/293,932, filed on Jan. 11, 2010, provisional application No. 61/346,476, filed on May 20, 2010.

(51) Int. Cl.
*A61B 1/32* (2006.01)
*A61B 17/34* (2006.01)
*A61B 1/00* (2006.01)
*A61M 1/00* (2006.01)
*A61B 17/24* (2006.01)
*A61B 17/00* (2006.01)

(52) U.S. Cl.
CPC ....... *A61B 17/3431* (2013.01); *A61B 1/00154* (2013.01); *A61B 1/32* (2013.01); *A61B 17/3423* (2013.01); *A61B 17/24* (2013.01); *A61B 2017/00278* (2013.01); *A61B 2017/00849* (2013.01); *A61B 2017/00876* (2013.01); *A61B 2017/345* (2013.01); *A61B 2017/3443* (2013.01); *A61B 2017/3447* (2013.01); *A61B 2217/005* (2013.01); *A61B 2217/007* (2013.01); *A61M 1/0084* (2013.01)

(58) Field of Classification Search
CPC ........... A61B 17/24; A61B 17/3421–17/2468; A61B 17/0218; A61B 2017/246; A61B 2017/248; A61B 2017/0225; A61B 1/233; A61B 1/32; A61M 2210/0618
See application file for complete search history.

(56) References Cited

U.S. PATENT DOCUMENTS 2,335,936 A    12/1943  Hanlon
3,568,678 A    3/1971   Pourquier et al.
(Continued)

OTHER PUBLICATIONS

United States Patent and Trademark Office, Non-final Office Action issued in U.S. Appl. No. 13/798,990 (May 13, 2014).
(Continued)

*Primary Examiner* — Jacqueline Johanas
(74) *Attorney, Agent, or Firm* — Kenneth H. Ohriner; Perkins Coie LLP

(57) ABSTRACT

A surgical sheath for use in endoscopic trans-nasal or intra-ocular surgery has first and second attachment fittings on opposite side of a conical section used for attaching individual sheaths to form a sheath pair. The sheaths of the pair can mutually support each other during surgery, to better resist inadvertent displacement of the sheaths. After the sheaths are positioned, the conical sections of the sheaths may be attached together using clips, pins, belts or other techniques. The sheaths reduce collateral trauma to the tissues in the surgical pathway.

16 Claims, 19 Drawing Sheets

(56) References Cited

U.S. PATENT DOCUMENTS

| | | | |
|---|---|---|---|
| 3,664,330 A | 5/1972 | Deutsch | |
| 3,867,946 A | 2/1975 | Huddy | |
| 4,280,493 A * | 7/1981 | Council | A61M 16/0666 128/201.18 |
| 4,312,353 A | 1/1982 | Shahbabian | |
| 4,755,174 A | 7/1988 | Milewski et al. | |
| 4,819,619 A * | 4/1989 | Augustine | A61M 16/0488 128/200.26 |
| 4,821,715 A * | 4/1989 | Downing | A61M 16/0461 128/200.26 |
| 4,883,465 A | 11/1989 | Brennan | |
| 5,011,474 A | 4/1991 | Brennan | |
| 5,139,510 A | 8/1992 | Goldsmith et al. | |
| 5,336,163 A | 8/1994 | DeMane et al. | |
| 5,400,770 A | 3/1995 | Nakao et al. | |
| 5,599,284 A | 2/1997 | Shea | |
| 5,601,591 A | 2/1997 | Edwards et al. | |
| 5,601,594 A | 2/1997 | Best | |
| 5,713,839 A | 2/1998 | Shea | |
| 5,800,394 A | 9/1998 | Yoon et al. | |
| 5,827,224 A * | 10/1998 | Shippert | A61B 17/12022 604/104 |
| 5,865,728 A | 2/1999 | Moll et al. | |
| 5,967,970 A | 10/1999 | Cowan et al. | |
| 5,993,407 A | 11/1999 | Moazed | |
| 6,033,426 A | 3/2000 | Kaji | |
| 6,083,155 A | 7/2000 | Trese | |
| 6,102,928 A | 8/2000 | Bonutti | |
| 6,183,493 B1 * | 2/2001 | Zammit | A61F 5/08 606/196 |
| 6,186,965 B1 | 2/2001 | Patterson | |
| 6,306,084 B1 | 10/2001 | Pinczower | |
| 6,309,345 B1 | 10/2001 | Stelzer et al. | |
| 6,328,753 B1 * | 12/2001 | Zammit | A61F 5/08 606/196 |
| 6,386,197 B1 | 5/2002 | Miller | |
| 6,454,783 B1 | 9/2002 | Piskun | |
| 6,607,546 B1 * | 8/2003 | Murken | A61B 17/12104 606/196 |
| 7,100,612 B2 * | 9/2006 | Dunlap | A61M 16/0461 128/200.26 |
| 7,361,168 B2 | 4/2008 | Makower et al. | |
| 7,410,480 B2 | 8/2008 | Muni et al. | |
| 7,520,876 B2 | 4/2009 | Ressemann et al. | |
| 7,654,997 B2 | 2/2010 | Makower et al. | |
| 7,678,099 B2 | 3/2010 | Ressemann et al. | |
| 7,720,521 B2 | 5/2010 | Chang et al. | |
| 7,727,186 B2 | 6/2010 | Makower et al. | |
| 7,730,888 B2 * | 6/2010 | Dunlap | A61M 16/0461 128/207.18 |
| 7,740,642 B2 | 6/2010 | Becker | |
| 7,753,929 B2 | 7/2010 | Becker | |
| 7,753,930 B2 | 7/2010 | Becker | |
| 7,771,409 B2 | 8/2010 | Chang et al. | |
| 7,799,337 B2 | 9/2010 | Levin | |
| 7,918,871 B2 * | 4/2011 | Truitt | A61B 17/12022 606/199 |
| 8,409,083 B2 | 4/2013 | Mangiardi | |
| 8,986,201 B2 * | 3/2015 | Chen | A61B 1/00154 600/201 |
| 9,004,071 B2 * | 4/2015 | Alexander | A61B 19/22 128/200.26 |
| 2002/0013511 A1 | 1/2002 | Ailinger et al. | |
| 2003/0014076 A1 | 1/2003 | Mollenauer et al. | |
| 2003/0154986 A1 | 8/2003 | Fariss et al. | |
| 2004/0138525 A1 | 7/2004 | Saadat et al. | |
| 2004/0210114 A1 | 10/2004 | Simon | |
| 2004/0230100 A1 | 11/2004 | Shluzas | |
| 2004/0243172 A1 | 12/2004 | Hogle | |
| 2005/0059960 A1 | 3/2005 | Simaan et al. | |
| 2005/0075540 A1 | 4/2005 | Shluzas et al. | |
| 2005/0165366 A1 | 7/2005 | Brustad et al. | |
| 2005/0240147 A1 * | 10/2005 | Makower | A61B 17/24 604/96.01 |
| 2006/0004323 A1 | 1/2006 | Chang et al. | |
| 2006/0169285 A1 * | 8/2006 | Bovo | A61M 16/0666 128/206.11 |
| 2006/0173407 A1 | 8/2006 | Shaughnessy et al. | |
| 2006/0200003 A1 | 9/2006 | Youssef | |
| 2006/0272640 A1 * | 12/2006 | Abullon | A61F 5/08 128/203.22 |
| 2006/0287583 A1 | 12/2006 | Mangiardi | |
| 2007/0005094 A1 | 1/2007 | Eaton et al. | |
| 2007/0016174 A1 | 1/2007 | Millman et al. | |
| 2007/0021773 A1 | 1/2007 | Nolte | |
| 2007/0100370 A1 | 5/2007 | Hogle | |
| 2007/0191876 A1 * | 8/2007 | Dubrul | A61F 5/56 606/199 |
| 2007/0203474 A1 | 8/2007 | Ryan et al. | |
| 2007/0219575 A1 | 9/2007 | Mejia | |
| 2007/0225568 A1 | 9/2007 | Colleran | |
| 2007/0277831 A1 | 12/2007 | Luhrs | |
| 2007/0277832 A1 * | 12/2007 | Doshi | A61M 15/08 128/207.18 |
| 2007/0293726 A1 | 12/2007 | Goldfarb et al. | |
| 2007/0299314 A1 | 12/2007 | Bertolero et al. | |
| 2008/0027464 A1 | 1/2008 | Moll et al. | |
| 2008/0045803 A1 | 2/2008 | Williams et al. | |
| 2008/0058590 A1 | 3/2008 | Saadat et al. | |
| 2008/0065105 A1 | 3/2008 | Larkin et al. | |
| 2008/0065108 A1 | 3/2008 | Diolaiti | |
| 2008/0071288 A1 | 3/2008 | Larkin et al. | |
| 2008/0097514 A1 * | 4/2008 | Chang | A61F 11/002 606/196 |
| 2008/0097516 A1 * | 4/2008 | Chang | A61F 11/002 606/196 |
| 2008/0109026 A1 | 5/2008 | Kassam | |
| 2008/0132938 A1 * | 6/2008 | Chang | A61F 11/002 606/196 |
| 2008/0188868 A1 | 8/2008 | Weitzner et al. | |
| 2008/0234550 A1 | 9/2008 | Hawkes et al. | |
| 2008/0243064 A1 | 10/2008 | Stahler et al. | |
| 2008/0255519 A1 | 10/2008 | Piskun et al. | |
| 2008/0275483 A1 * | 11/2008 | Makower | A61B 17/24 606/192 |
| 2009/0010991 A1 | 1/2009 | Prabhu et al. | |
| 2009/0054728 A1 | 2/2009 | Trusty | |
| 2009/0062927 A1 | 3/2009 | Marten et al. | |
| 2009/0095303 A1 * | 4/2009 | Sher | A61M 16/06 128/207.18 |
| 2009/0137952 A1 | 5/2009 | Ramanurthy et al. | |
| 2009/0248057 A1 * | 10/2009 | Kotler | A61M 16/0666 606/199 |
| 2009/0312745 A1 | 12/2009 | Goldfarb et al. | |
| 2010/0030031 A1 | 2/2010 | Goldfarb et al. | |
| 2010/0076555 A1 | 3/2010 | Marten et al. | |
| 2010/0100181 A1 | 4/2010 | Makower et al. | |
| 2010/0145147 A1 | 6/2010 | Pinsky et al. | |
| 2010/0174149 A1 | 7/2010 | Moll et al. | |
| 2010/0174308 A1 | 7/2010 | Chang et al. | |
| 2010/0179537 A1 | 7/2010 | Rashidi | |
| 2010/0211181 A1 * | 8/2010 | Prabhu | A61F 2/04 623/23.7 |
| 2010/0228227 A1 | 9/2010 | Krespi et al. | |
| 2010/0249523 A1 | 9/2010 | Spiegal et al. | |
| 2010/0298862 A1 | 11/2010 | Chang et al. | |
| 2010/0331777 A1 | 12/2010 | Danielsson | |
| 2011/0004194 A1 | 1/2011 | Eaton et al. | |
| 2011/0005529 A1 * | 1/2011 | Doshi | A61M 15/08 128/848 |
| 2011/0048430 A1 * | 3/2011 | Arnon | A24F 47/00 128/848 |
| 2011/0118551 A1 | 5/2011 | Ciporen et al. | |
| 2011/0125092 A1 | 5/2011 | Hepworth et al. | |
| 2013/0092173 A1 * | 4/2013 | Alexander | A61B 19/22 128/207.18 |
| 2013/0096374 A1 * | 4/2013 | Alexander | A61B 19/22 600/102 |

(56) References Cited

U.S. PATENT DOCUMENTS

| | | | |
|---|---|---|---|
| 2013/0190571 A1* | 7/2013 | Chen | A61B 1/00154 600/204 |
| 2015/0164552 A1* | 6/2015 | Chen | A61B 17/3496 600/204 |
| 2015/0216561 A1* | 8/2015 | Alexander | A61B 19/22 600/204 |
| 2015/0250973 A1* | 9/2015 | Allum | A61M 16/0666 128/205.25 |

OTHER PUBLICATIONS

United States Patent and Trademark Office, Non-final Office Action issued in U.S. Appl. No. 14/626,184 (Oct. 2, 2015).

United States Patent and Trademark Office, Non-final Office Action issued in U.S. Appl. No. 13/369,952 (Jul. 26, 2013).

United States Patent and Trademark Office, Final Office Action issued in U.S. Appl. No. 13/369,952 (Jan. 21, 2014).

United States Patent and Trademark Office, Non-final Office Action issued in U.S. Appl. No. 12/943,779 (May 9, 2012).

United States Patent and Trademark Office, Final Office Action issued in U.S. Appl. No. 12/943,779 (Sep. 25, 2012).

United States Patent and Trademark Office, Non-final Office Action issued in U.S. Appl. No. 12/943,779 (Jul. 26, 2013).

United States Patent and Trademark Office, Final Office Action issued in U.S. Appl. No. 12/943,779 (Dec. 20, 2013).

Korean Intellectual Property Office, International Search Report issued in PCT Publication No. WO11/060125 A3 (Jul. 28, 2011).

* cited by examiner

SURGICAL TISSUE PROTECTION SHEATH

This application claims priority to U.S. Provisional Patent Application No. 61/730,588 filed Nov. 28, 2012. This application is also a Continuation-in-Part of U.S. patent application Ser. No. 13/798,990 filed Mar. 13, 2013, now U.S. Pat. No. 8,986,201. Application No. 61/730,588; Ser. Nos. 13/760,971; 13/789,990; and 12/943,779 are incorporated herein by reference.

BACKGROUND OF THE INVENTION

Endoscopic surgery within the head is a common procedure in neurological surgery and otolaryngology. It avoids large cranial incisions and can reduce the need brain retraction and prolonged wound healing. Endoscopic surgery within the head also provides improved illumination and visualization of the target tissues because the camera of the endoscope is brought directly to the surgical site.

During this type of surgery, there may be local trauma to the tissues in the surgical pathway, resulting from pressure or abrasion caused by the surgical instruments. Generally these tissues are the nasal mucosa, turbinates, nasal septum, and sphenoid/frontal/maxillary sinus. When transorbital approaches are used, orbital and periorbital tissue are subject to local trauma. Surgical pathway trauma can add to the trauma of the procedure and prolong the patient's recovery time. Liquids in the surgical pathway, such as mucous, blood, and soiled irrigation fluid, tend to obscure the view of the endoscope. This leads to the constant need for irrigation and suction of the obstructing liquids. In some cases the endoscope may also have to be removed, cleaned and replaced multiple times during a single procedure. This disadvantage tends to increase the complexity and time requirements of the operation. In addition, with each movement of a surgical tool into or out of the surgical pathway, the surrounding tissues are put at risk of additional trauma. Improved devices and methods are therefore needed.

SUMMARY OF THE INVENTION

A surgical sheath for use in endoscopic trans-nasal or intra-ocular surgery has first and second attachment fittings on opposite side of a conical section used for attaching individual sheaths to form a sheath pair. The sheaths of the pair can mutually support each other during surgery, to better resist inadvertent displacement of the sheaths. After the sheaths are positioned, the conical sections of the sheaths may be attached together using clips, pins, belts or other techniques. The sheaths reduce collateral trauma to the tissues in the surgical pathway.

BRIEF DESCRIPTION OF THE DRAWINGS

In the drawings, the same reference number indicates the same element in each of the views.

DETAILED DESCRIPTION OF THE DRAWINGS

Figure 2:
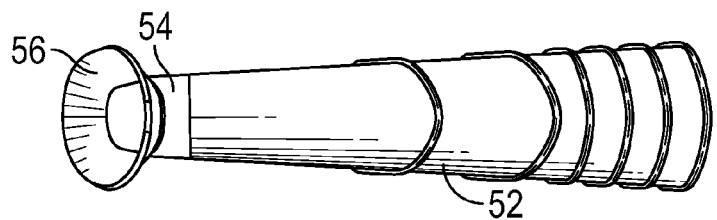
FIG. 2 is a bottom view of the sheath shown in FIG. 1.
Figure 3:
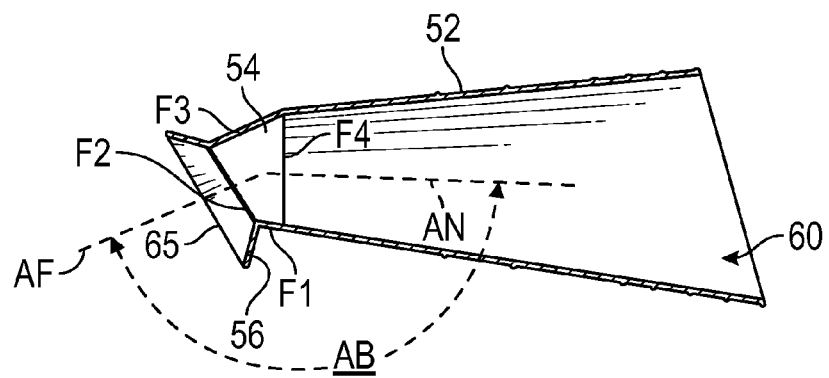
FIG. 3 is a section view of the sheath shown in FIG. 1.
Figure 4:
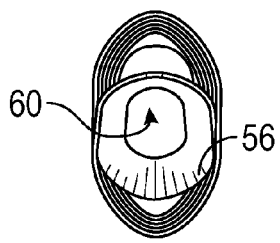
FIG. 4 is left end view of the sheath of FIG. 1.
Figure 5:
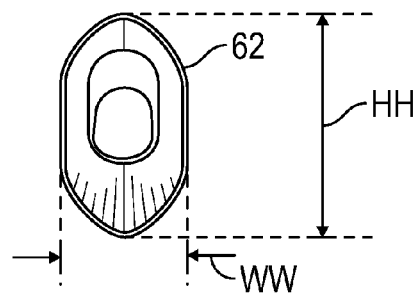
FIG. 5 is a right end view of the sheath of FIG. 1.
Figure 6:
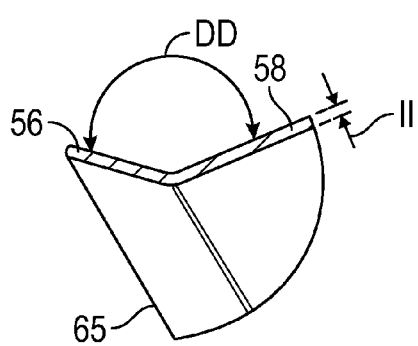
FIG. 6 is an enlarged detail view of detail A shown in FIG. 3.
Figure 7:
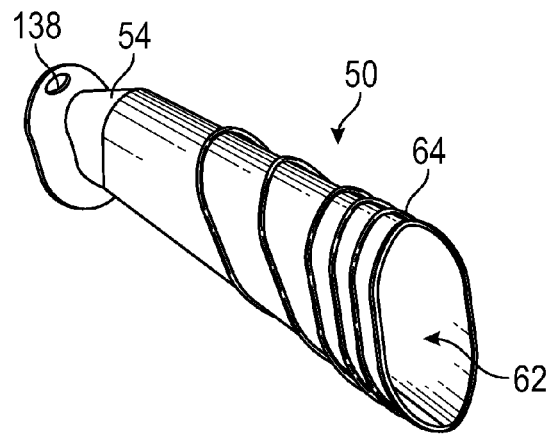
FIG. 7 is front, top and right side perspective view of the sheath shown in FIG. 1.
Figure 8:
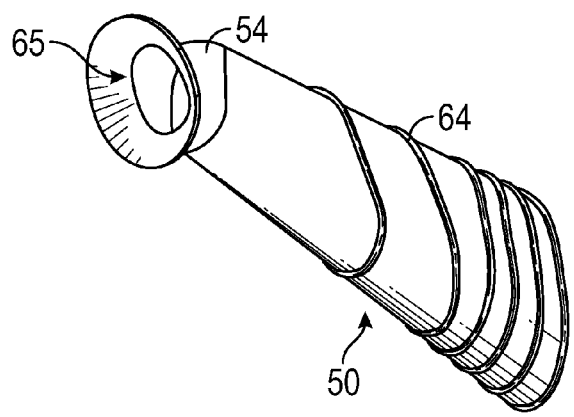
FIG. 8 is rear, bottom and right side perspective view of the sheath shown in FIG. 1.

FIGS. 1-8 show a first design for a sheath 50 having a body section 52, and angle section 54 and a flare or conical section 56. The sheath 50 may be molded of rubber or plastic as a one piece unit with the body section 52, the angle section 54 and the flare section integrally joined together. As shown in FIG. 6, the sheath 50 may have a thin flexible wall 58 having a thickness TT typically ranging from about 0.1 to 1 mm, or 0.2 to 0.8 mm. The flare section 56 may be provided as a conical ring forming an angle DD of 120-160 or 130-150 degrees with the top wall of the angle section. The sheath 50 may have a single through passageway 60 extending from a distal opening 62 to a proximal opening 65. As shown in FIGS. 4, 5 and 8, the openings 62 and 65, and the cross section of the body 52, may be generally in the shape of an oval or an ellipse.

Figure 1:
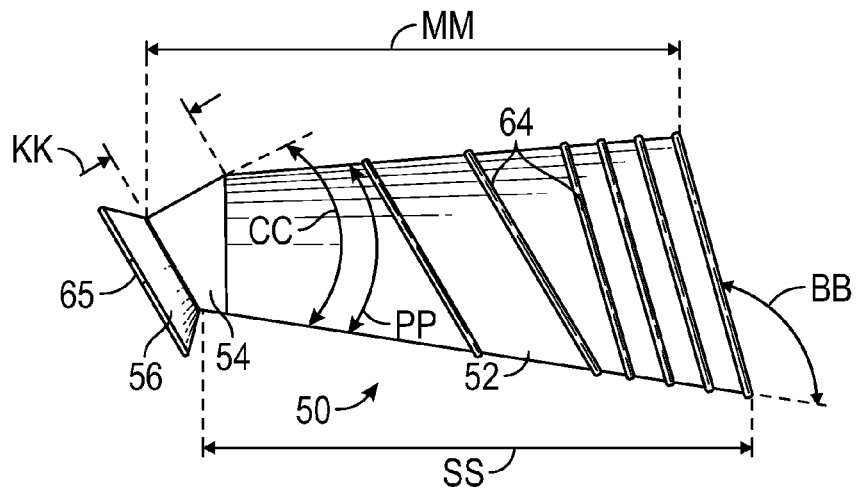
FIG. 1 is a side view of a tissue protection sheath.

Referring to FIGS. 1 and 3, the distal opening 62 may lie in a plane forming an angle forming an angle BB with the bottom of the sheath, with BB ranging from 95 to 125 or 100 to 115 degrees. As best shown in FIG. 3, the angled section 54 may be described as joined to the body section 52 at a vertical line 51. The upper and lower walls of the sheath extend distally away from the vertical line 51 towards the distal opening 62 at acute angles to the line 51, which may the same or different angles. As shown in FIG. 1, the included angle CC between the top surface of the angled section 54 and the lower wall of the body section may range from 25 to 40 or 30 to 35 degrees. The angle PP in FIG. 1 relating to the diverging angle of the top and bottom surfaces of the body section is typically 10-20 or 12-16 degrees. Dimension KK may be 8-16 or 10-14 mm, with dimensions MM and SS both generally about 65-85 or 70-80 mm.

For some procedures the sheath 50 may be provided as a cut-to-length unit. For example, the sheath may be provided in a sterile package, and have a length up to about 100 mm, with the surgeon cutting off a section of the front or distal end 62, to obtain a desired length. Scale markings (inches or millimeters) may optionally be printed or molded on an outside surface of the sheath for this purpose.

Turning to FIGS. 1-2 and 7-8, one or more ridges 64 may be provided on an outer surface of the body section 52. The ridges 64 may project up by 0.5 to 3 mm above the nominal outer surface of the sheath 50. A cluster of 2-5 ridges 64 may be provided near the distal opening 52, as shown in FIGS. 1 and 2. These ridges 64 may be parallel to each other, and optionally also parallel to the plane of the distal opening 52. Additional ridges 64, oriented at an angle of e.g., 10-20 or 13-17 degrees, may be provided more centrally on the body section 52 of the sheath 50. The ridges may optionally be provided as rings extending continuously around the outside surface of the body section.

Optionally, one or more spring or elastic elements 66, such as a spring wire 66, may be attached to or embedded in the sheath 50, to help expand the sheath from a folded or collapsed position into and expanded deployed position, after the sheath is positioned in the surgical pathway. The elastic element 66 may be a Nitinol wire. The dimensions and angles shown in the drawings of all embodiments may typically be varied by 10, 20 or 30% depending on various design parameters.

The angle section 54 may allow the proximal end of the sheath 50 to be more easily stretched and/or deflected. This allows for more versatile movement of surgical instruments extending through the sheath during surgery. As shown in FIGS. 1 and 3, the angle section 54 forms an irregular quadrilateral shape in cross section. In FIG. 3, the angle section 54 may be defined by line F4 along with segments or lines F1, F2 and F3, with F4 and F2 forming a first acute angle and with F1 and F3 forming a second acute angle. Each of the sides or segments F4, F1, F2 and F3 forming the angle section 54 may also have different lengths. F3 may be substantially perpendicular to F2. The angle section 54 may alternatively be described via a centerline AN perpendicular to and bisecting segment or line F4 and intersecting a centerline AF of the conical section 54 at an angle AB of 5-30 or 10-20 degrees.

The wall thickness of the sheath 50 may be thinner at the proximal end adjacent to the flare 56, to allow the proximal end to more easily stretch. For example, the sheath 50 shown in FIGS. 1-8 may be 6 to 10 cm long with the proximal 10 to 30% of the length having a reduced wall thickness in comparison to the rest of the sheath. The wall thickness of this section may be 20 to 80 or 30 to 70% of the regular wall thickness of the rest of the sheath. The wall thickness may optionally be largely uniform with all sections of the sheath having a similar thickness TT.

Figure 12:
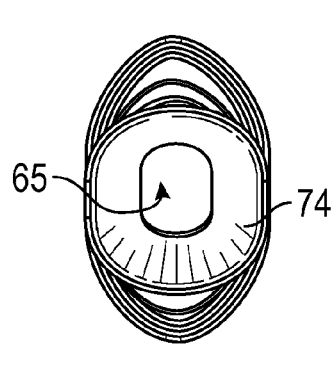
FIG. 12 is left end view of the sheath of FIG. 9.
Figure 13:
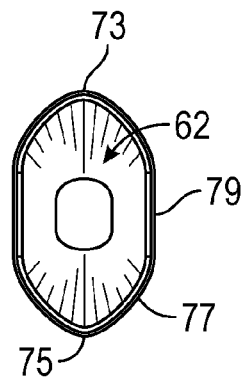
FIG. 13 is a right end view of the sheath of FIG. 9.
Figure 14:
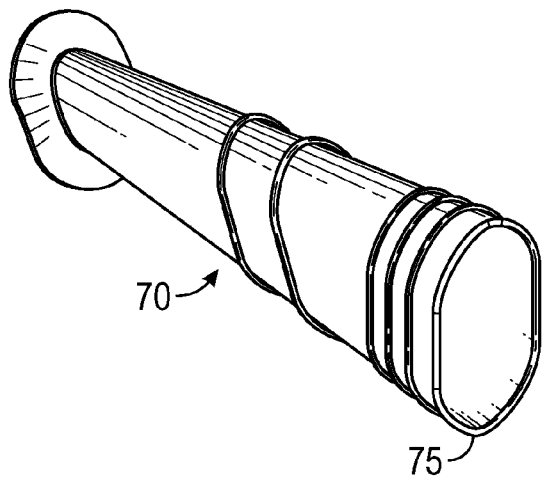
FIG. 14 is front, top and right side perspective view of the sheath shown in FIG. 9.

FIGS. 9-15 show a second design 70 similar to the sheath 50 but without the angle section 54. As with the sheath 50, the sheath 70 may have distal and proximal openings oriented in non-parallel planes. The sheath 70 may have a flare end 74 that is flatter than the flare end 56 on the sheath 50, with the flare end 74 at an angle EE to the centerline of 50 to 70 or 55 to 65 degrees, and with angle FF typically ranging from 8 to 15 degrees. The outer diameter GG of the flare end 74 may be 22-30 or 24-28 mm, with the outer diameter of the front end generally about 16-22 mm. The sheath 70 may also have a longer and narrower through passageway, as shown in FIG. 12. Comparing FIG. 13 to FIG. 3 shows that the body section of the sheath 70 may be symmetrical about the centerline 71 while the body section of the sheath 50 is not similarly symmetrical.

Figure 9:
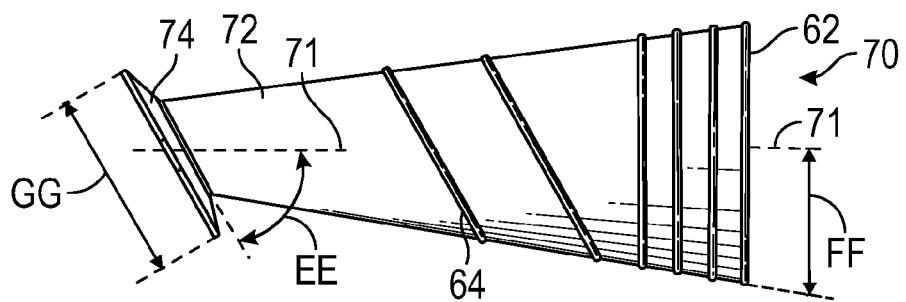
FIG. 9 is a side view of a second embodiment of a tissue protection sheath.
Figure 10:
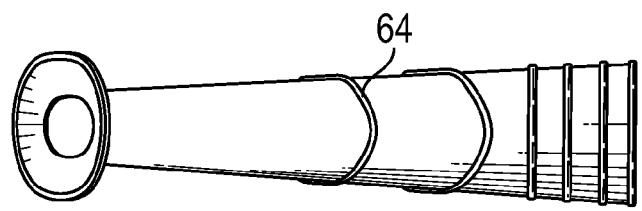
FIG. 10 is a bottom view of the sheath of FIG. 9.
Figure 11:
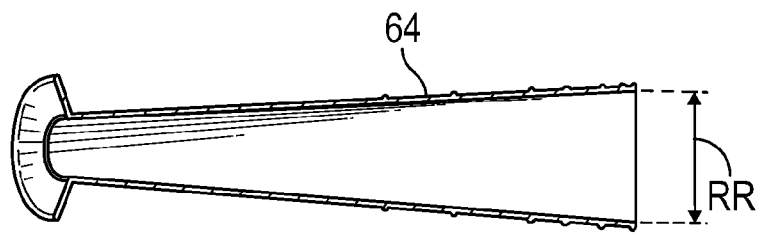
FIG. 11 is a centerline section view of the sheath of FIG. 9.
Figure 15:
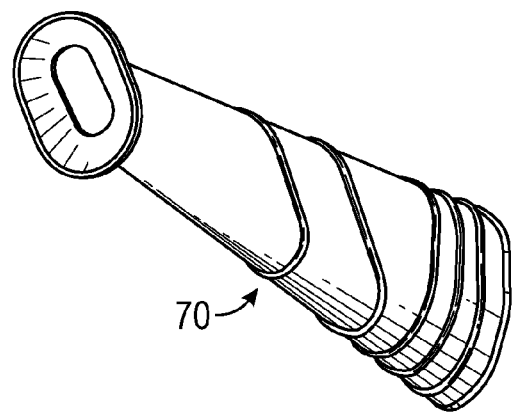
FIG. 15 is rear, bottom and right side perspective view of the sheath shown in FIG. 9.
Figure 16:
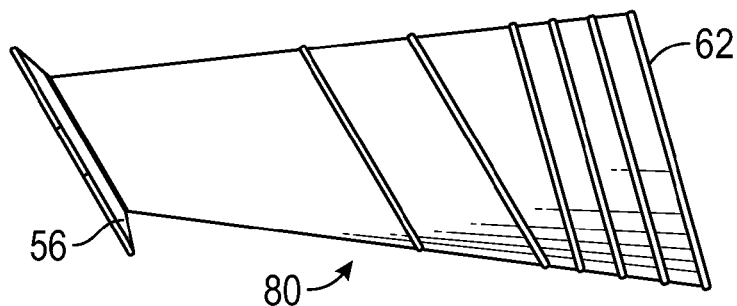
FIG. 16 is a side view of a third embodiment of a tissue protection sheath.
Figure 17:
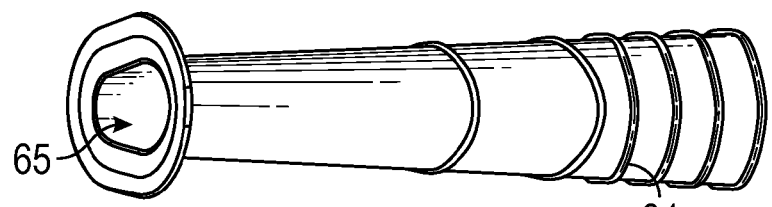
FIG. 17 is a bottom view of the sheath shown in FIG. 9.
Figure 18:
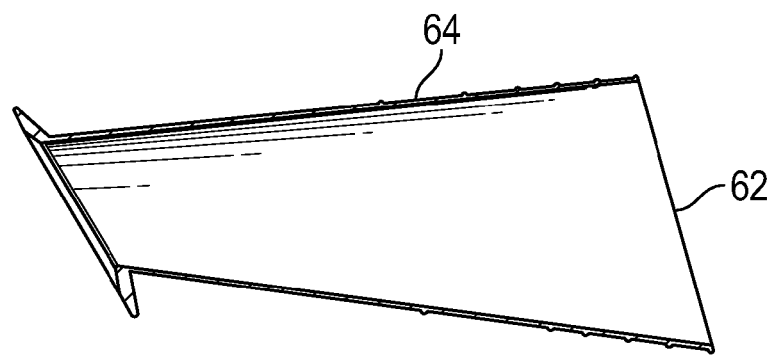
FIG. 18 is a section view of the sheath of FIG. 16 taken along a centerline.

As shown in FIGS. 9 and 13, the body section of the sheath 70 and/or the distal opening 62 may have upper and lower creases 73 and 75 having a radius of 2 mm or less, with curved sidewalls 77 leading from the creases to a substantially flat center sidewall 79. As shown in FIGS. 12 and 15, the proximal opening 65 may be an oval.

Figure 19:
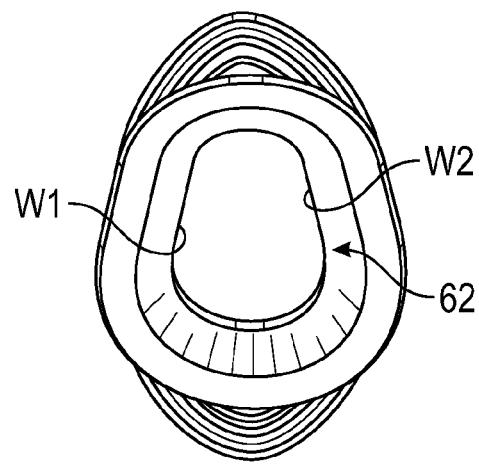
FIG. 19 is left end view of the sheath of FIG. 15.
Figure 20:
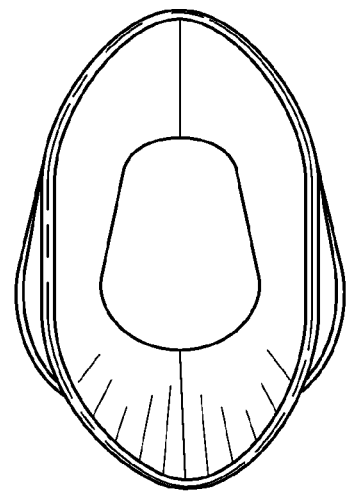
FIG. 20 is a right end view of the sheath of FIG. 15.
Figure 21:
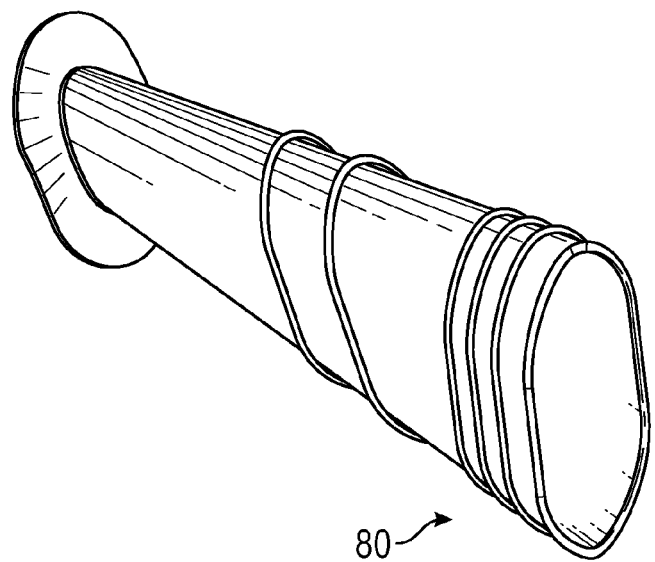
FIG. 21 is front, top and right side perspective view of the sheath shown in FIG. 15.
Figure 22:
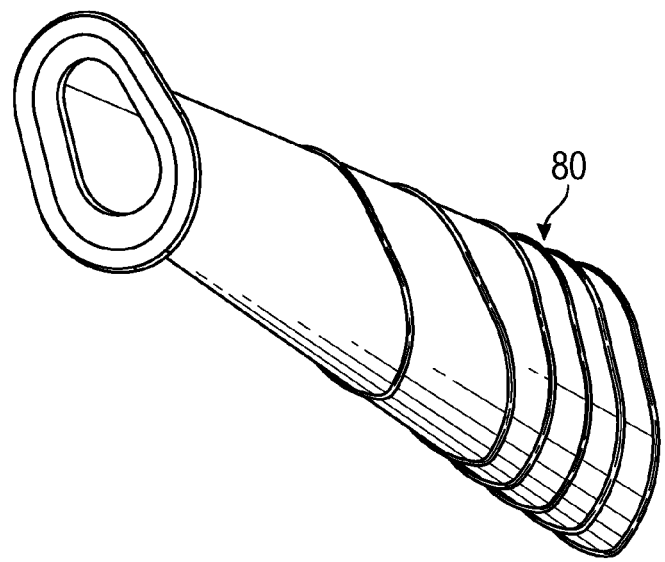
FIG. 22 rear, bottom and right side perspective view of the sheath shown in FIG. 15.

FIGS. 16-22 show a third design 80 that is similar to the sheath 70 but having a distal opening 62 in a plane forming an acute angle with a longitudinal centerline of the body section, similar to FIG. 1, as opposed to the perpendicular distal opening orientation in FIG. 9. As shown in FIG. 19 the proximal opening 62 may have non-parallel sidewalls upwardly converging sidewalls W1 and W2 joined by a smaller radius of curvature at the top and a larger radius of curvature at the bottom, in the form of a teardrop or an uneven oval. In each of the sheaths described, the body section may be at least 2, 4, 6, 8 or 10 times longer than the conical section, or the combined length of the conical section and the angle section, if used.

Figure 23:
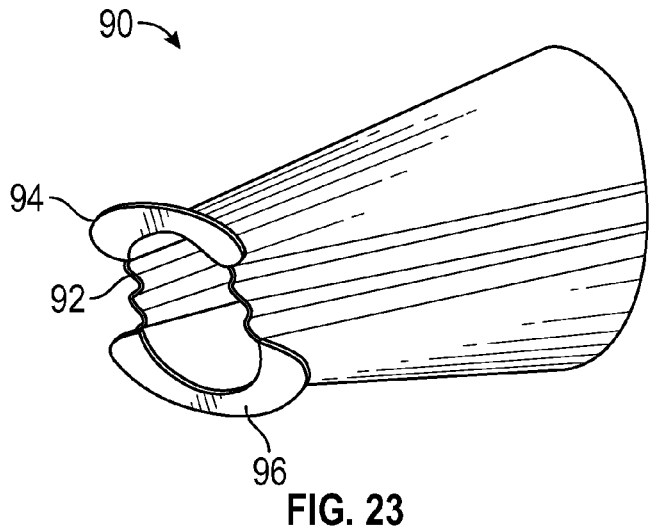
FIG. 23 is rear, top and right side perspective view of another sheath design.

FIG. 23 shows a similar design further including pleats or folds 92 at the proximal end. The flare end may also be split into an upper section 94 and a lower section 96, with no flare section overlying the pleats 92. This allows the proximal end of the sheath 90 to more easily stretch open to better accommodate manipulation of surgical tools. The pleats 92 may be molded into the proximal end of the sheath 90, with the pleats reducing and blending into the body section of the sheath towards the distal end of the sheath 90. The wall thickness at the pleats may be reduced to e.g., 0.2-0.7 mm, to allow the pleats to stretch with nominal force.

Figure 24:
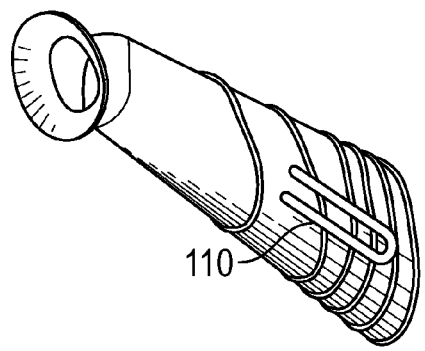
FIG. 24 rear, top and right side perspective view of a sheath similar to the sheath of FIG. 1 and further including side pockets.

FIG. 24 shows a sheath which may be similar or the same as the sheaths 50, 70 or 80, and further including pockets 110 on opposite sides configured to accept the jaws of a bayonet forceps. The pockets may help the forceps to grasp and hold the sheath, and also allow the sheath to be pushed forward using the forceps, but without excessively clamping or squeezing the sheath.

Figure 25:
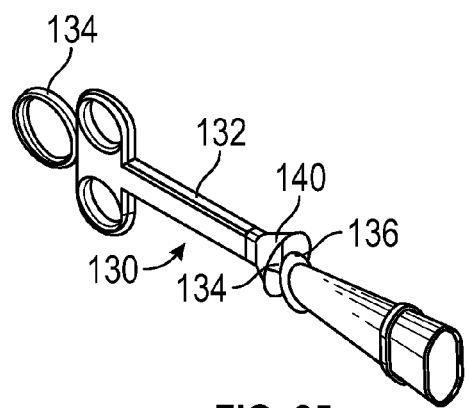
FIG. 25 is a side view of a sheath delivery tool.

FIG. 25 shows a sheath deployment tool 130 that may be used to deploy a sheath. The tool 130 has a plunger 134 slidable into a handle 132. A hook 136 or other grasping feature on the plunger 134 engages a hook slot 138 on the sheath, with the hook slot 138 shown in FIG. 1. Funnel guides 140 may be provided on the handle 132 to collapse down and guide the sheath into the handle. The tool 130 may then be used to place the sheath into a surgical pathway.

Figure 26:
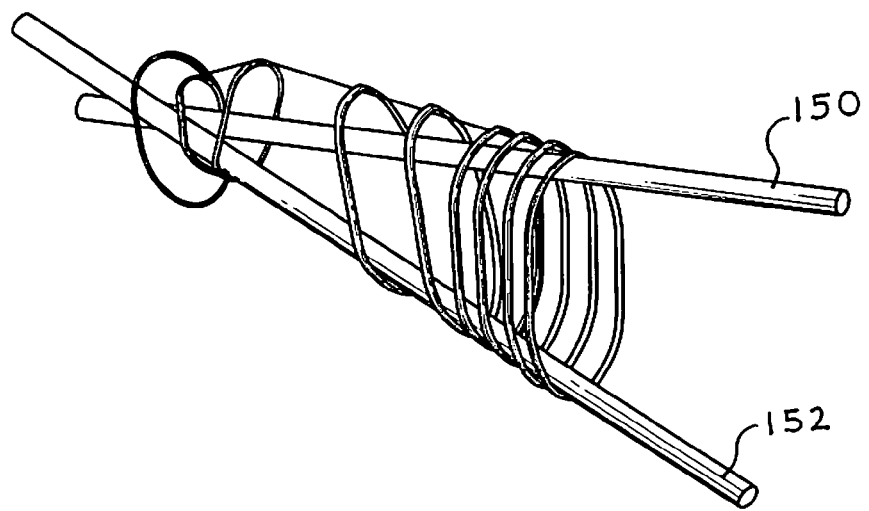
FIG. 26 is a rear, top and right side perspective view of the sheath of FIG. 1 with surgical instruments schematically illustrated in use.
Figure 27:
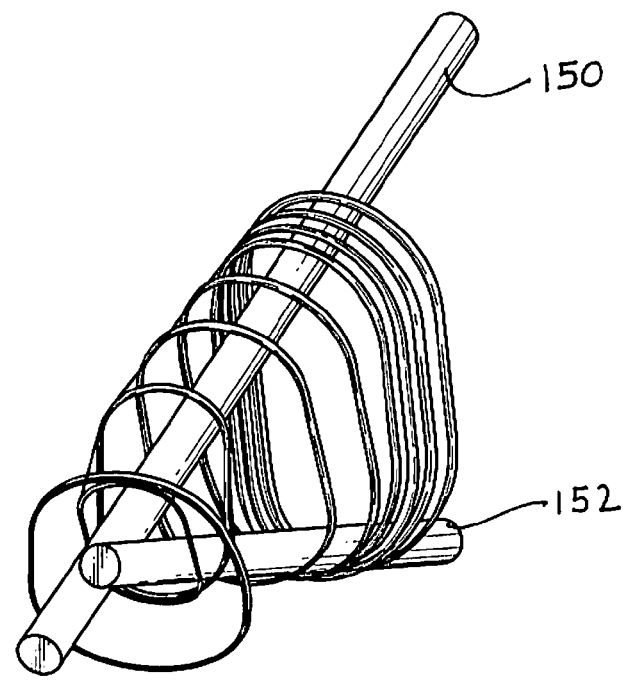
FIG. 27 is a front, top and right side perspective view of the sheath and surgical instruments as shown in FIG. 26.

FIGS. 26 and 27 show two surgical tools 150 and 152 in use with the sheath. As the sheath tapers outwardly from the proximal opening 65 to the distal opening 62, clashing of the instruments may be reduced as the sheath provides more room for the instruments to move at a distance from the leverage point of the nostril.

FIGS. 28-45 show sheath pairs which may formed in different ways. In general, the conical section of each sheath in these designs has a first attachment fitting on a first side of the conical section and a second attachment fitting on a second side of the conical section, with the first and second attachment fittings used to attach the sheaths to form a sheath pair.

Figure 28:
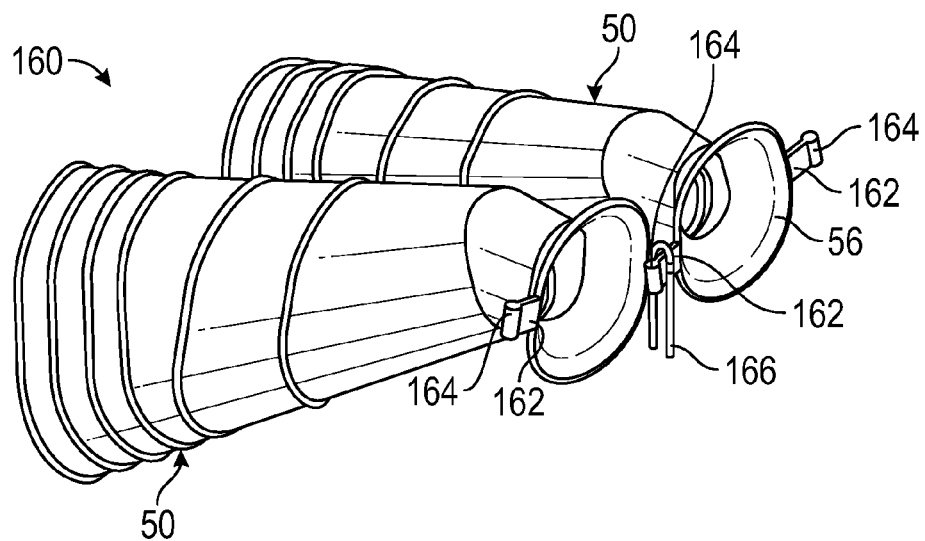
FIG. 28 is a front, top and left side perspective view of a pair of sheaths attached together via a U-pin.
Figure 29:
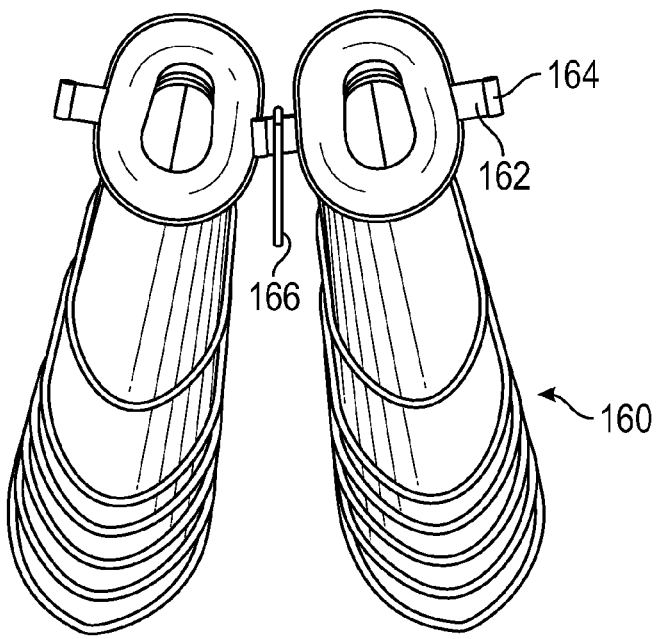
FIG. 29 is a front and bottom perspective view of the sheaths of FIG. 28.
Figure 30:
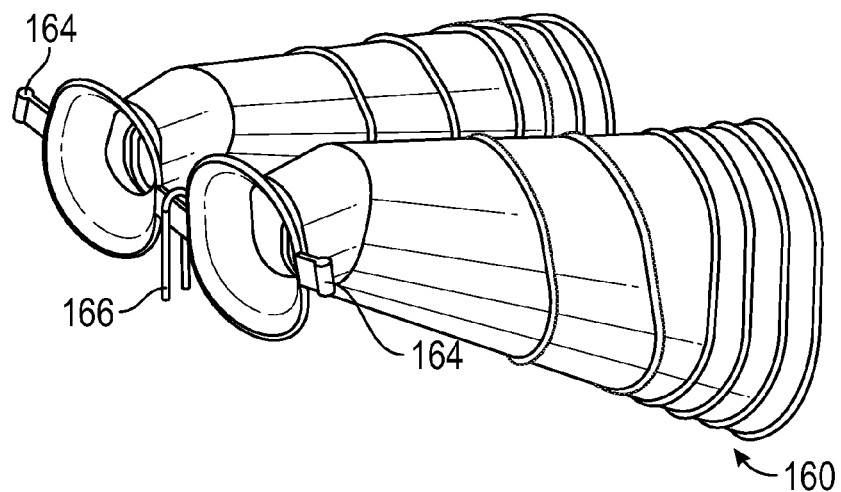
FIG. 30 is front, top and right side perspective view of the sheaths of FIG. 28.

FIGS. 28 to 30 show two sheaths attached together to form a pair of sheaths 160. Each sheath of the pair 160 may be the same as the sheath 50, with side tabs 162 added onto opposite sides of the conical section 56. Each tab 162 may have a flat rectangular section having an inner end joined to the conical section 56, and cylindrical end 164 on the outer end of the tab. The sheaths 50 may be attached together by overlapping the tabs 162, and clamping them via a U-pin or clip 166, as shown in FIG. 29.

Generally, the side tabs 162 may be integrally molded components of the conical section 56. The conical section 56 may be provided with a greater wall thickness than the body section 52, to better resist pulling forces that may be exerted on the side tabs 162. For example, with a rubber sheath, the body section 52 may have a wall thickness of 0.5 mm with the conical section having a wall thickness of 0.7 to 1.0 mm. The side tabs 162 may be centered vertically on the conical section 56, i.e., with dimension LL in FIG. 29 equal to one half of the total height of the conical section.

In use, the sheaths 50 of the pair 160 as shown in FIGS. 28-30 are placed for surgery as described above. The sheaths 50 may then be attached together via sliding the clip 166 over the overlapping side tabs 162. The clip 166 may be provided as a spring clamp, with the legs momentarily pulled apart when installing the clip 166 onto the side tabs 162, and with the legs thereafter exerting a spring clamping force on the side tabs 162. When attached together as shown in FIGS. 28-30, the conical sections of each sheath mutually support each other, helping to keep the sheaths in position.

Figure 31:
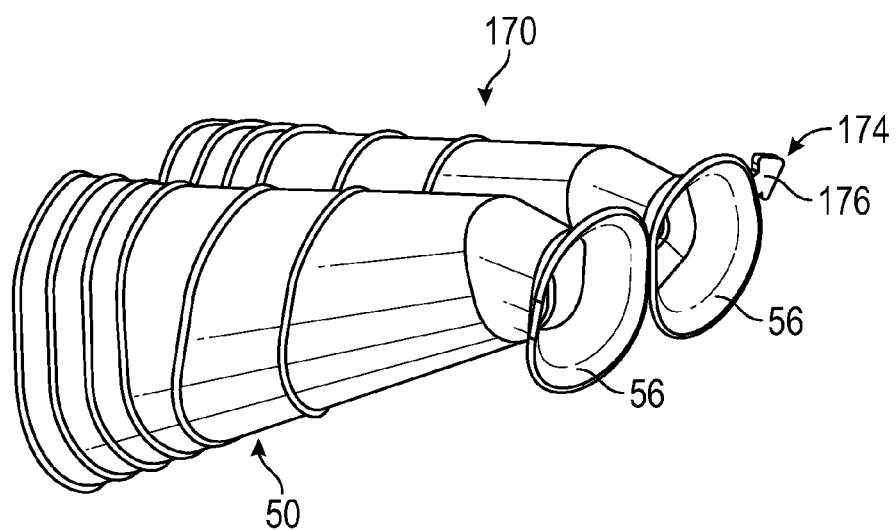
FIG. 31 is a front, top and left side perspective view of a pair of sheaths attached together via an arrow hook.
Figure 32:
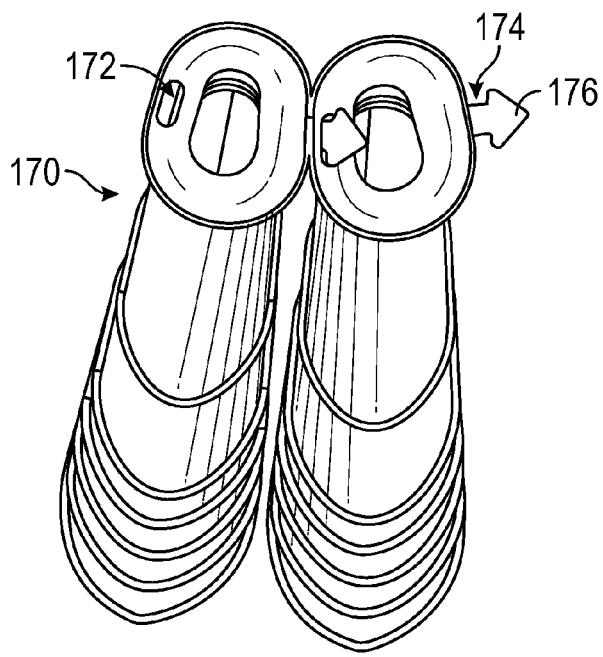
FIG. 32 is a front and bottom perspective view of the sheaths of FIG. 31.
Figure 33:
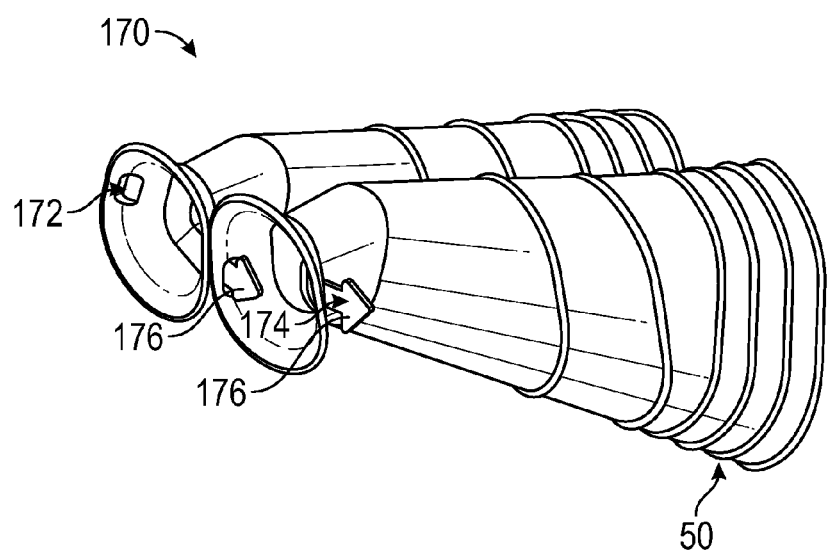
FIG. 33 is front, top and right side perspective view of the sheaths of FIG. 31.

FIGS. 31-33 show a sheath pair 170 similar to the sheath pair 160 in FIGS. 28-30, but with a side tab 174 having an arrowhead 176 which may be pushed through a slot or hole 172 in the conical section.

Figure 34:
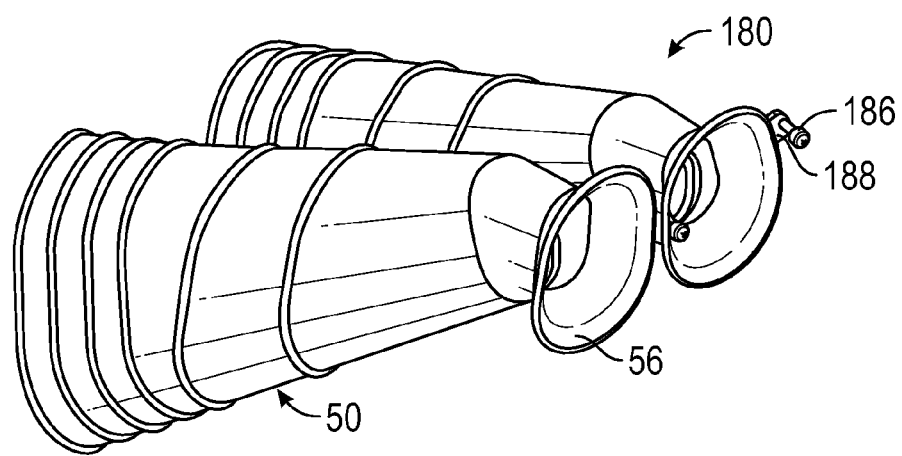
FIG. 34 is a front, top and left side perspective view of a pair of sheaths attached together via a push-through pin.
Figure 35:
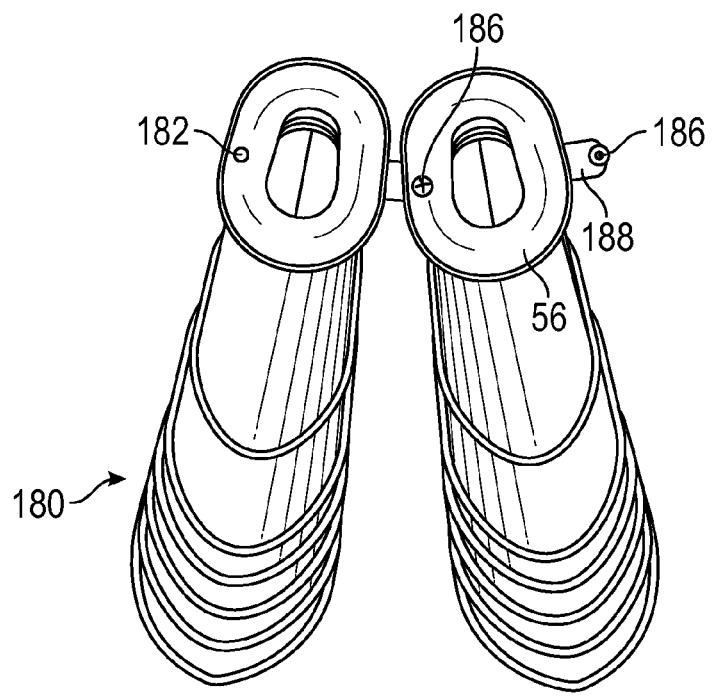
FIG. 35 is a front and bottom perspective view of the sheaths of FIG. 34.
Figure 36:
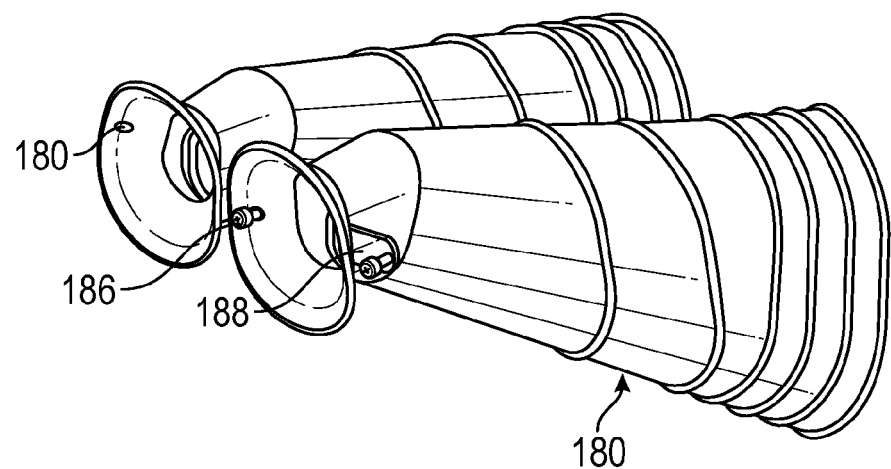
FIG. 36 is front, top and right side perspective view of the sheaths of FIG. 34.

FIGS. 34-36 show a sheath pair 180 similar to the sheath pair 160 in FIGS. 28-30, but with a side tab 174 having a plug pin 184 having a head 186 which may be pushed through a slot or hole 180 in the conical section. The head 186 is nominally larger in diameter than the hole 180, with the resilient material of the plug pin and/or the conical section allowing the head 186 to be pushed through the hole, and then retained.

Figure 37:
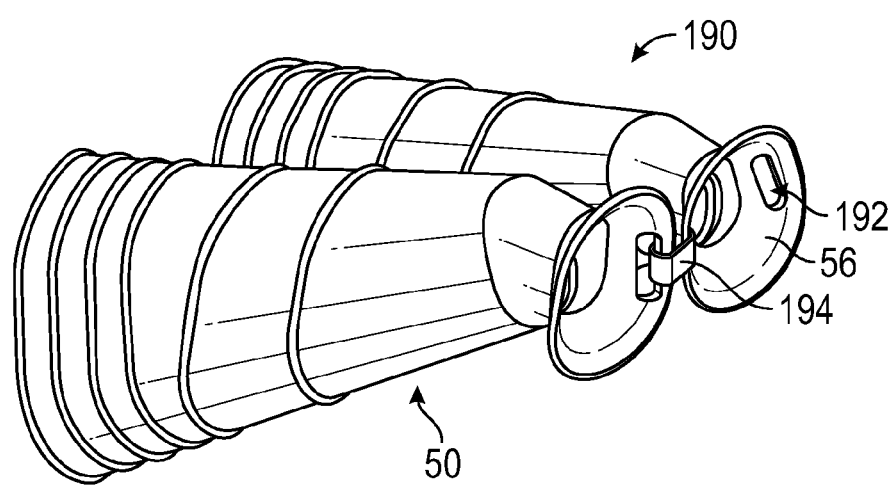
FIG. 37 is a front, top and left side perspective view of a pair of sheaths attached together via a loop strap.
Figure 38:
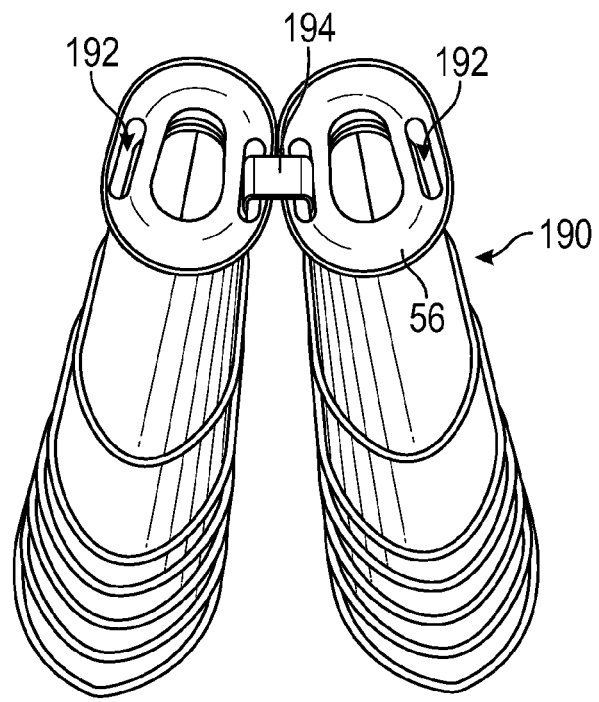
FIG. 38 is a front and bottom perspective view of the sheaths of FIG. 37.
Figure 39:
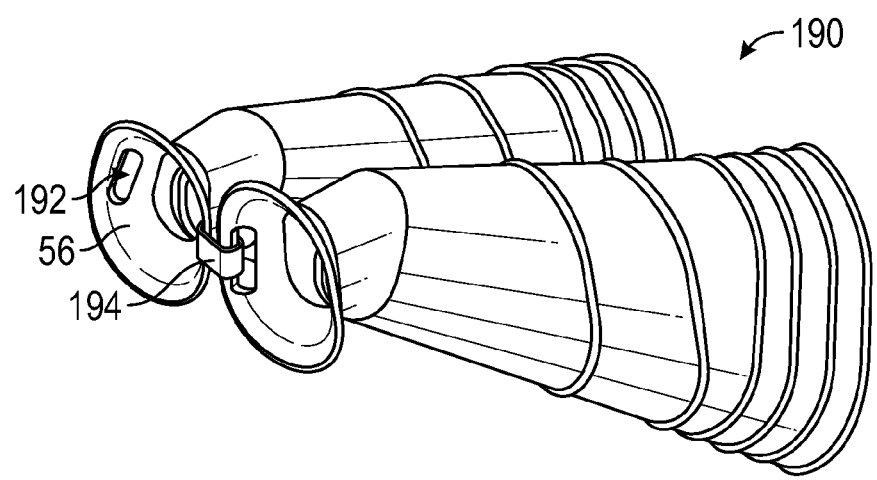
FIG. 39 is front, top and right side perspective view of the sheaths of FIG. 37.

FIGS. 37-39 show a sheath pair 190 similar to the sheath pair 160 in FIGS. 28-30, but with slots or holes 192 on both sides of the conical section 56, and with a belt 194 looped through the slots 192. The belt 194 may be a length of cord, suture, tape, zip-tie, Velcro hook and loop tape, or fabric looped through the slots and then knotted. The belt 194 may optionally be provided as a metal or plastic spring clip or snap ring.

Figure 40:
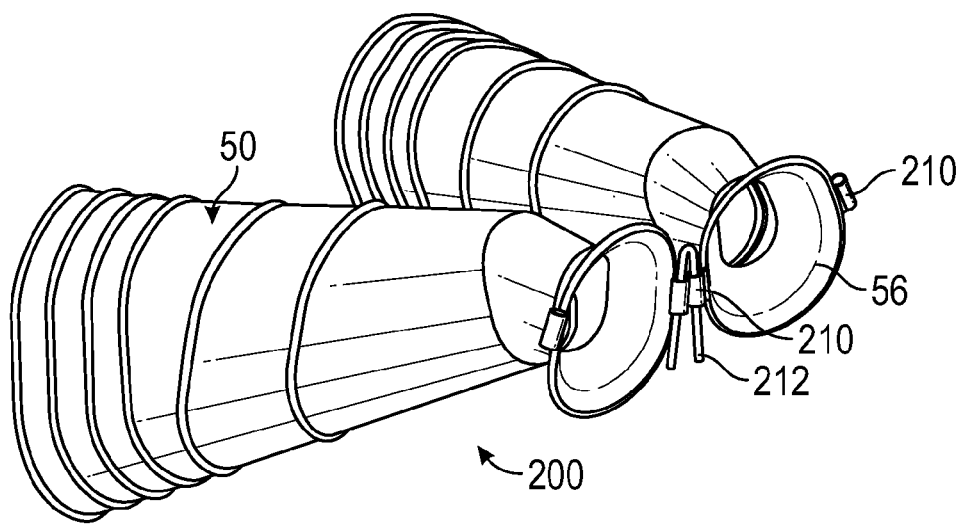
FIG. 40 is a front, top and left side perspective view of a pair of sheaths attached together via a V-pin.
Figure 41:
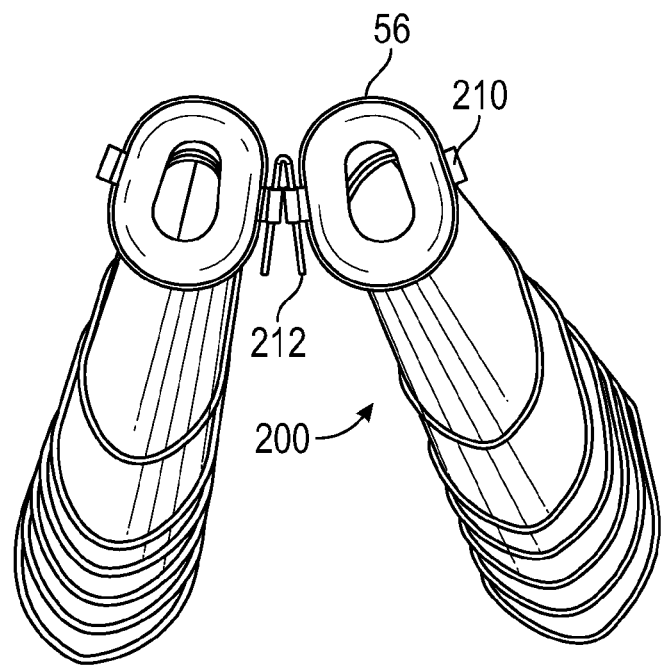
FIG. 41 is a front and bottom perspective view of the sheaths of FIG. 40.
Figure 42:
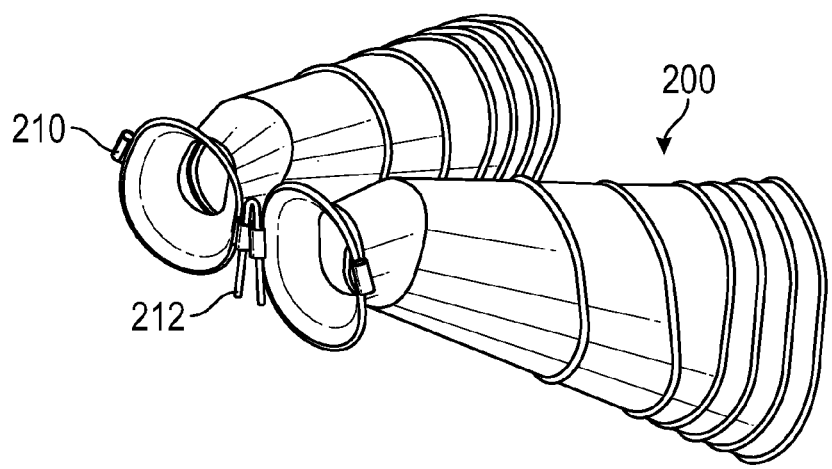
FIG. 42 is front, top and right side perspective view of the sheaths of FIG. 40.

FIGS. 40-42 show a sheath pair 200 similar to the sheath pair 160 in FIGS. 28-30, but with pin collars 210 on opposite sides of the conical section 56, with each pin collar having a through hole. A V-clip or a U-clip 212 has a leg inserted through adjacent pin collars 210 to attach the sheaths together.

Figure 43:
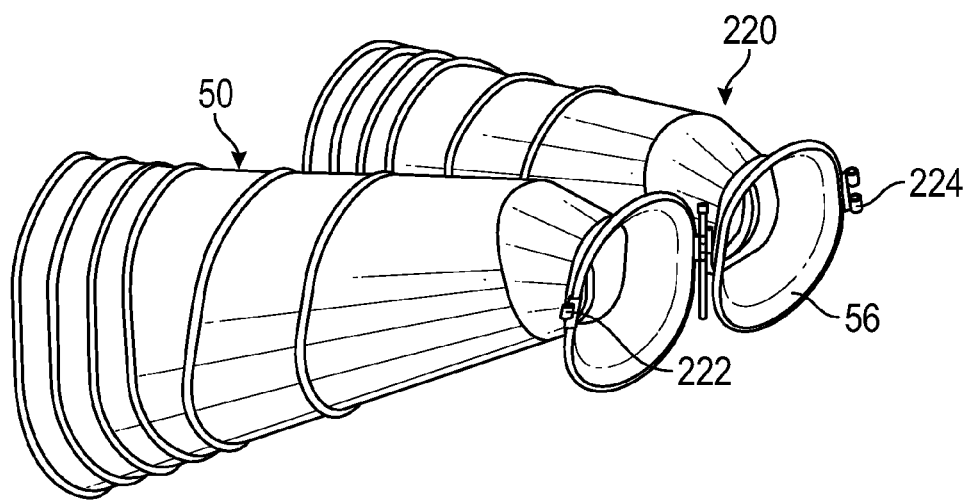
FIG. 43 is a front, top and left side perspective view of a pair of sheaths attached together via a straight pin.
Figure 44:
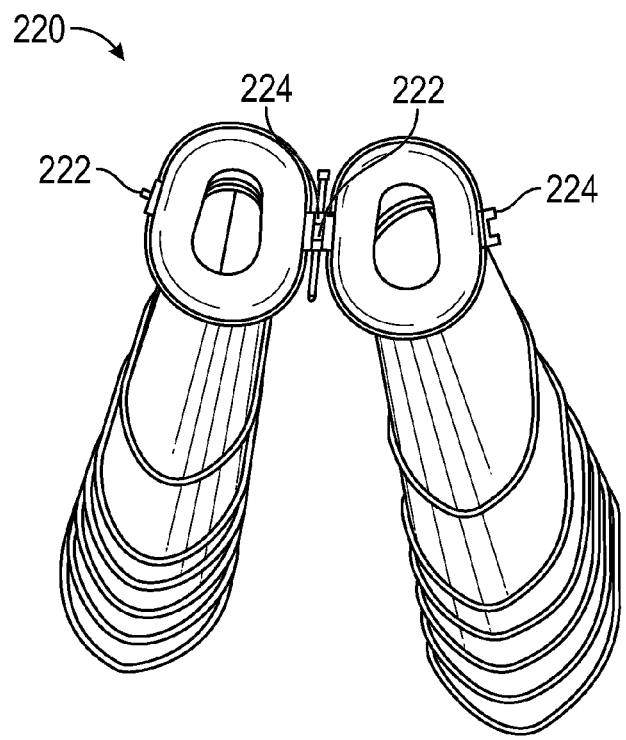
FIG. 44 is a front and bottom perspective view of the sheaths of FIG. 43.
Figure 45:
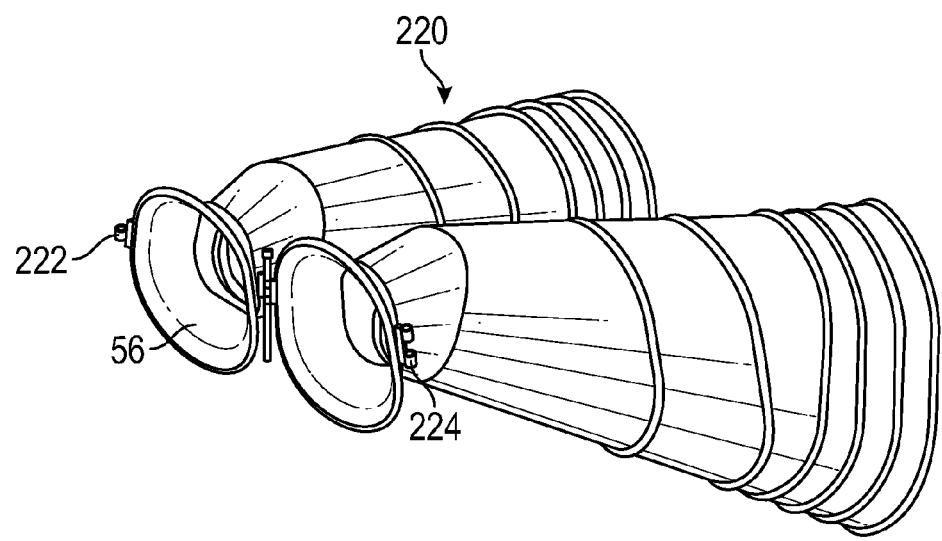
FIG. 45 is front, top and right side perspective view of the sheaths of FIG. 43.

FIGS. 43-45 show a sheath pair 220 similar to the sheath pair 160 in FIGS. 28-30, but with a right collar 222 and a left collar 224 on opposite sides of each conical section 56. The right collar 222 may have one or more hinge knuckles vertically offset from hinge knuckles of the left collar 224, allowing through holes in the collars to align. A straight pin having a head may then be inserted through the interlaced adjacent collars 222 and 224 to attach the sheaths together.

Figure 46:
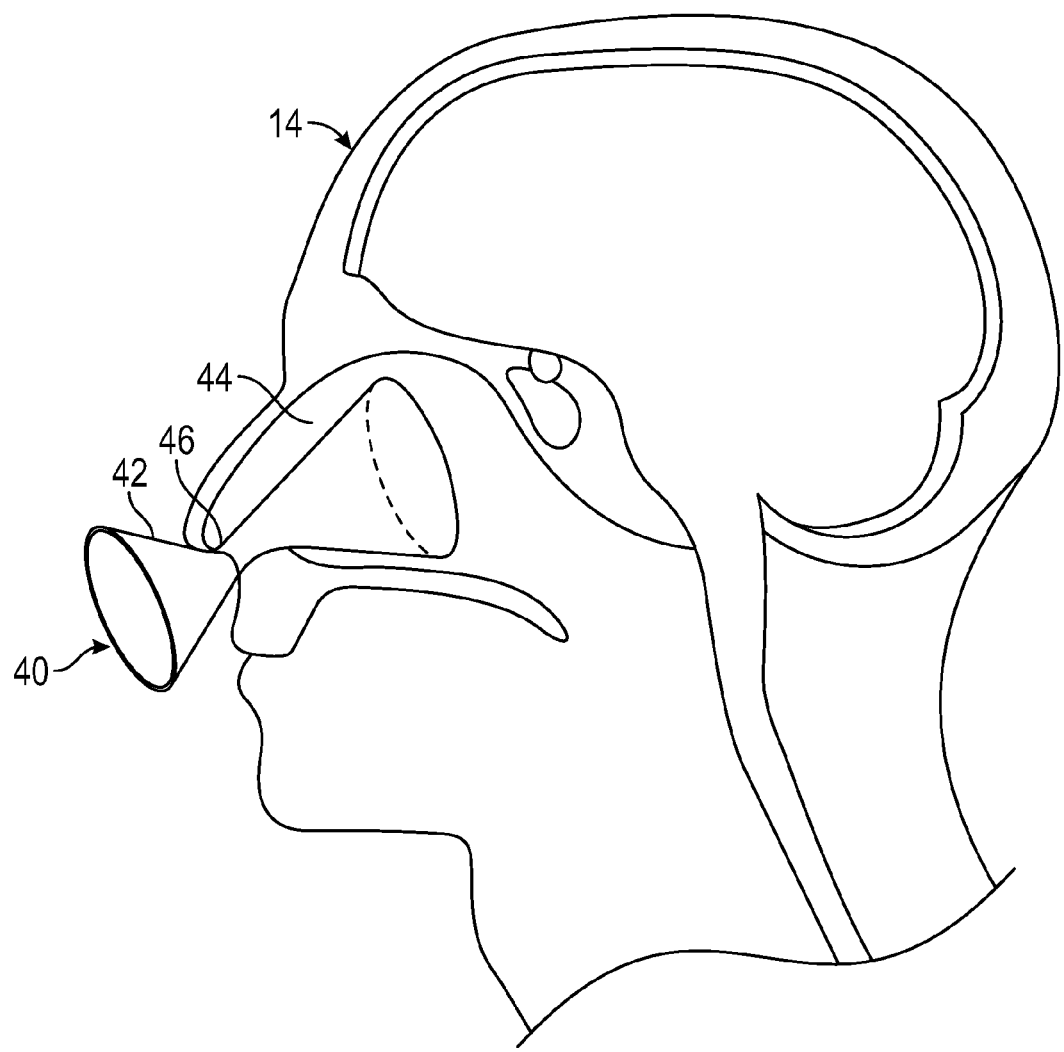
FIG. 46 is sectional view of a human head and a sheath deployed in a nostril of the human head.

FIG. 46 illustrates a sheath 40 within a human head 14. The sheath 40 has a flared proximal portion 42 and a flared distal portion 44. A reduced dimension section 46 joins the portions 42 and 44 and serves to hold the device 40 in place during the surgery.

The features of the pair 160 as described above also apply to the pairs 170, 180, 190, 200 and 210. Although generally the sheaths 50 are provided separately and then attached after positioned within the nose, in some applications the sheath pairs described above may be provided via two sheaths that are permanently attached together, with no pins or belts needed. Of course the other sheaths 70, 80 and 90 described above may similarly be used in a pair as shown in FIGS. 28-45. Other forms of attachment may also be used to attach the conical sections, such as suturing, clamping, snaps, buttons or adhesives. The sheaths may be symmetrical to allow them to be used interchangeably in either the right nostril or the left nostril, while still attachable to each other.

The sheaths described above are useful in transnasal and transorbital surgery of the head. The sheaths may also be used in other surgical procedures for protection of tissue around a surgical pathway. The sheaths above are discussed in terms of having different sections only for purposes of description. The sheaths may be manufactured from rubber or plastic as an integral one-piece unit, without specific or visible separation lines or features between the sections described. As used here, vertically or vertical means in the up/down direction in the drawings.

Thus, novel surgical sheaths and sheath pairs have been shown and described. Various changes and substitutions may of course be made without departing from the spirit and scope of the invention. The invention, therefore, should not be limited except by the following claims and their equivalents.

The invention claimed is:

1. A surgical method comprising:
   A.) providing a first sheath, and a second sheath unattached to the first sheath:

B.) inserting a first body section of the first sheath into a first nostril of a patient, with the first sheath having a first conical section joined to the first body section, and with the first conical section outside of the first nostril;

C.) after performing step B, inserting a second body section of the second sheath into a second nostril of the patient, with the second sheath having a second conical section joined to the second body section, and with the second conical section outside of the second nostril; and D.) after performing step C, attaching the first conical section of the first sheath to the second conical of the second sheath;

E.) after performing step D, moving a first surgical instrument through the first sheath.

2. The method of claim 1 comprising attaching the first conical section of the first sheath to the second conical section of the second sheath by routing a belt through openings in the first and second conical sections.

3. The method of claim 2 wherein the belt comprises suture, further comprising routing the suture through the first conical section and through the second conical section, and knotting the suture.

4. The method of claim 2 wherein the belt comprises suture.

5. The method of claim 4 further comprising knotting the suture.

6. The method of claim 1 wherein the first sheath is identical to the second sheath.

7. The method of claim 1 wherein the first and second conical sections are thicker than the first and second body sections, respectively.

8. The method of claim 1 with the first and second conical sections flaring outwardly from the first and second nostrils, respectively.

9. The method of claim 1 further comprising moving a second surgical instrument through the second sheath.

10. The method of claim 1 with the first conical section having a first conical section diverging angle, and with the first body section having a first body section diverging angle less than the first conical section diverging angle; and with the second conical section having a second conical section diverging angle, and with the second body section having a second body section diverging angle less than the second conical section diverging angle.

11. A surgical method comprising:

A.) providing a first sheath, and a second sheath unattached to the first sheath;

B.) inserting a first body section of the first sheath into a first nostril of a patient, with the first sheath having a first conical section joined to the first body section, and with the first conical section outside of the first nostril, and with the first conical section having a first conical section diverging angle, and with the first body section having a first body section diverging angle less than the first conical section diverging angle;

C.) after performing step B, inserting a second body section of the second sheath into a second nostril of the patient, with the second sheath having a second conical section joined to the second body section, and with the second conical section outside of the second nostril, with the second conical section having a second conical section diverging angle, and with the second body section having a second body section diverging angle less than the second conical section diverging angle;

D.) after performing step C, routing a suture through the first and second conical sections and knotting the suture to attach the first conical section of the first sheath to the second conical of the second sheath; and E.) after performing step D, positioning a first surgical instrument through the first sheath.

12. The method of claim 11 further comprising routing the suture through a first hole in the first conical section and through a second hole in the second conical section.

13. The method of claim 11 wherein the first and second conical sections are thicker than the first and second body sections, respectively.

14. The method of claim 11 further comprising positioning a second surgical instrument through the second sheath.

15. The method of claim 11 wherein the first conical section is joined to the first body section at an acute angle.

16. The method of claim 11 with the first and second conical sections flaring outwardly from the first and second nostrils, respectively.

* * * * *